(12) United States Patent
Boury et al.

(10) Patent No.: US 8,367,114 B2
(45) Date of Patent: Feb. 5, 2013

(54) METHOD FOR PREPARING PARTICLES FROM AN EMULSION IN SUPERCRITICAL OR LIQUID $CO_2$

(75) Inventors: Frank Boury, Angers (FR); Jean-Pierre Benoit, Angers (FR); Olivier Thomas, Angers (FR); Frédéric Tewes, Poitiers (FR)

(73) Assignee: Institut National de la Sante et de la Recherche Medicale (INSERM), Paris (FR)

( * ) Notice: Subject to any disclaimer, the term of this patent is extended or adjusted under 35 U.S.C. 154(b) by 1081 days.

(21) Appl. No.: 12/158,492

(22) PCT Filed: Dec. 22, 2005

(86) PCT No.: PCT/IB2005/003869
§ 371 (c)(1),
(2), (4) Date: Oct. 9, 2008

(87) PCT Pub. No.: WO2007/072106
PCT Pub. Date: Jun. 28, 2007

(65) Prior Publication Data
US 2009/0087491 A1    Apr. 2, 2009

(51) Int. Cl.
*A61K 9/14*    (2006.01)
(52) U.S. Cl. ........ 424/489; 424/490; 424/491; 424/497; 264/4.1

(58) Field of Classification Search ................... 424/489
See application file for complete search history.

(56) References Cited

U.S. PATENT DOCUMENTS

| | | | |
|---|---|---|---|
| 5,344,930 A | 9/1994 | Reiss et al. | |
| 6,063,138 A | 5/2000 | Hanna et al. | |
| 6,183,783 B1 | 2/2001 | Benoit et al. | |
| 2003/0077297 A1* | 4/2003 | Chen et al. | ..................... 424/400 |
| 2004/0156911 A1 | 8/2004 | Chattopadhyay et al. | |
| 2005/0220751 A1* | 10/2005 | Charmot et al. | ............. 424/78.1 |

FOREIGN PATENT DOCUMENTS

CN    1709224    12/2005

OTHER PUBLICATIONS

Plata et al, Formation of Ethyl Acetate and Isoamyl Acetate by Various Species of Wine Yeasts, Food Microbiology, vol. 20, Issue 2, pp. 217-224 (2003).*

\* cited by examiner

*Primary Examiner* — Frederick Krass
*Assistant Examiner* — Dennis J Parad
(74) *Attorney, Agent, or Firm* — B. Aaron Schulman, Esq.; Stites & Harbison, PLLC

(57) ABSTRACT

The present invention relates to a method for preparing particles, notably particles encapsulating an active substance. It also relates to particles obtainable by this process, dispersion thereof, and their use as a vehicle for pharmaceutical, cosmetic, diagnostic, veterinary, phytosanitary active substances or processed foodstuff.

21 Claims, 1 Drawing Sheet

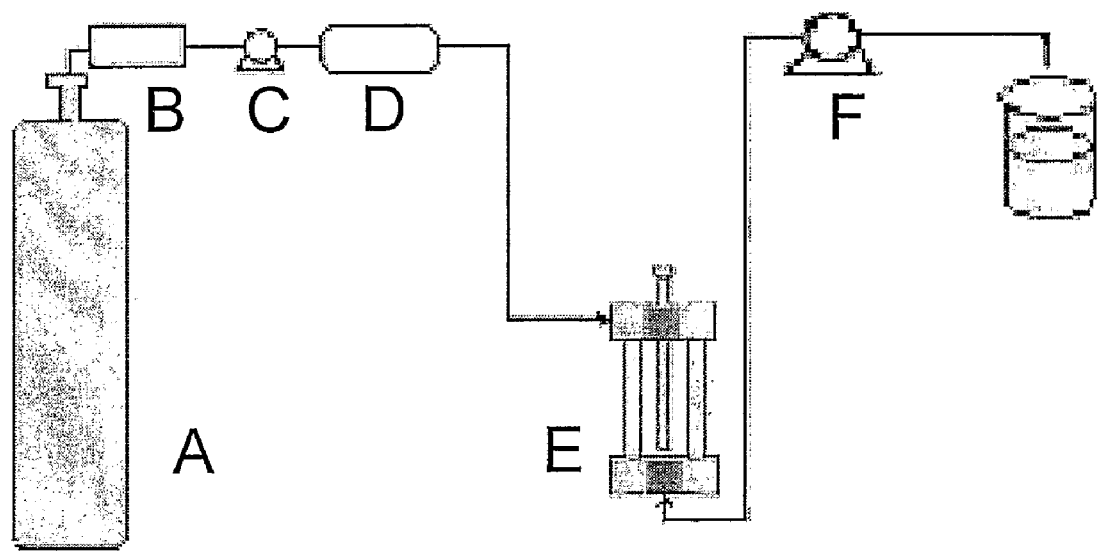

METHOD FOR PREPARING PARTICLES FROM AN EMULSION IN SUPERCRITICAL OR LIQUID CO₂

The present invention relates to a method for preparing particles, notably particles encapsulating an active substance.

It also relates to particles obtainable by this process, dispersion thereof and their use as a charge or as a vehicle for pharmaceuticals, cosmetics, diagnostic compositions or processed foodstuff.

The encapsulation of substances into micro or nanoparticles has received an increased interest over the last years for various applications in diverse fields like medicine, chemistry, cosmetics, or nutrition. For instance, in the pharmaceutical field, the incorporation of the pharmacologically active molecules into microspheres allows to control their spatial and temporal delivery into the human body and permits to protect them against degradation.

The encapsulation processes used in pharmaceutical industry must take into account several requirements such as the stability of the active molecules, the yield and the efficiency of the drug encapsulation, the reproducibility of the microspheres quality and of the drug release profile, and the residual level of organic solvent in the microparticles, which should be lower than the limit value imposed by the Pharmacopoeia.

However, the common techniques used by the pharmaceutical industry to encapsulate active molecules, like emulsification-solvent removal, polymer phase-separation, spray drying and milling methods are not always suitable to formulate particles within these requirements (Arshady et al., 1991; Benoit et al., 1996). They often use harsh formulation conditions, which can induce physical or chemical changes in the active substances, especially if it is a protein, and lead to amounts of residual solvent that are difficult to decrease under the upper authorized values. In fact, the volatile organic chemicals (VOC), usually used in these processes, are subject to very strict international regulations (*ICH Harmonized Tripartite Guideline for Residual Solvents*, 1997), due to their toxicity for humans and for the environment.

Therefore, in the need to find new encapsulation methods, which offer a good encapsulation yield, do not damage the structure of the active substances and do not use any organic solvents, some researches are oriented to alternative methods, such as working with compressed carbon dioxide instead of the organic solvents. As a matter of fact, the carbon dioxide is non-toxic, non-flammable, abundant, recyclable, environmentally friendly and it has a tunable solvent power when it is close to its critical point (Tc=31.1° C. and Pc=73.8 bar). Due to its properties, it is neither regulated as a VOC, and nor restricted in food or pharmaceutical applications. All these advantages made compressed $CO_2$ an attractive solvent that offers a "green" alternative to the traditional organic solvents already used in a lot of processes such as extraction (Saldana et al., 2002), separation (Mendes et al., 2003; Ozcan et al., 2004), fractionation, cleaning (Campbell et al., 2001), reaction medium (Jacobson et al., 1999; Kane et al., 2000) or phase for emulsions-microemulsions (Psathas et al., 2002; Eastoe et al., 1997; Hoefling et al., 1991; Lee et al., 1999).

Consequently, the researches on the properties and possible applications of the compressed $CO_2$ have rapidly progressed over the last ten years. In this respect, much research has been done on water-carbon dioxide (W—C) binary systems (Eastoe et al., 1997, Bartscherer et al., 1995; Harrison et al., 1994; da Rocha et al., 2003; Johnston et al., 2001; Psathas et al., 2000; Ryoo et al., 2003; Zielinski et al., 2004), as they offer the advantage of acting as "universal" solvents, due to their binary composition allowing the dissolution of either polar or low molecular weight apolar substances.

Among the methods for preparing particles using supercritical or pressurised fluids, mention may be made of (i) technique using the supercritical fluids (hereafter called SF) as a solvent to solubilize active and/or carrier molecules, such as the Rapid Expansion of Supercritical Solution (RESS) technique, (ii) techniques using the SF as an antisolvent, where it is brought into contact with an organic solution to induce precipitation of the active molecules and/or the carrier, such the Gas Anti-Solvent (GAS) and Supercritical Anti-Solvent (SAS) related techniques, and (iii) techniques using the SF as a spray enhancer such as the techniques named Particles from Gas Saturated Solutions (PGSS), Polymer Liquefaction Using Supercritical Solvation (PLUSS), Supercritical-Assisted Atomization (SAA), Depressurization of an Expanded Liquid Organic solution (DELOS), $CO_2$-Assisted Nebulization and Bubble Drying (CAN-BD).

Thus, RESS process can be used when the substance of interest is highly soluble in the supercritical phase. The substance is dissolved in the supercritical phase and the formed solution is expanded rapidly by depressurizing the system through a heated nozzle, so that the substance precipitates as very small particles.

The GAS and SAS processes can be used for crystallization of substances which are not or only slightly soluble in the supercritical fluid. For the GAS processes, the substance of interest is dissolved in the organic solvent. When the supercritical fluid, which has a low solvent capacity with respect to the solute(s) but is completely miscible with the organic solvent, is added to a batch of the organic solution, the solute(s) precipitates in particles because the $CO_2$-expanded solvent has a lower solvent strength than the pure solvent.

For the SAS processes, the organic solution is sprayed through a nozzle, producing small solvent droplets, into a vessel filled of $CO_2$. Then, the $CO_2$ expands the solvent of the droplets, leading to formation of particles. Several adaptations of the SAS processes have been performed such as the ASES, PCA and the Solution Enhanced Dispersion by supercritical fluid (SEDS) process.

Micronization of proteins and polymer microparticles has been prepared according to these methods.

The principle of the processes using $CO_2$ as a spray enhancer consists in dissolving supercritical $CO_2$ (hereafter called $SCCO_2$) in melted substance(s) or in a solution/suspension of substances and depressurising this mixture through a nozzle, causing the formation of solid particles or liquid droplets. These processes allow particles to form from melt polymers that are not soluble in $SCCO_2$, but which absorb a large amount of $CO_2$ (1-30 wt %) (Tomasko D. L. et al., 2003).

However, these methods of processing materials using supercritical fluids hardly make it possible to control the morphology and the size of the obtained particles. Finally, a large number of these methods further uses organic co-solvents that may raise environmental and safety problems.

The aim of the present invention is to provide a method for preparing particles having a controlled size and morphology without the use of toxic organic solvent.

Thus, in one aspect, the invention is directed to a method for preparing particles comprising the steps of:
i) preparing an emulsion containing
as a continuous phase, supercritical or liquid $CO_2$, and
as a discontinuous phase, a solvent containing a substance selected from the group consisting of a polymer, a cationic divalent ion or a mixture thereof;

said substance being soluble in said solvent and insoluble in said continuous phase;

ii) solidifying said discontinuous phase, thereby forming particles.

The inventors have now demonstrated that it is possible to obtain spherical and uniform size particles by emulsifying a solution of a substance selected from the group consisting of a polymer, a cationic divalent ion or a mixture thereof in liquid or supercritical $CO_2$, before the solidification phenomenon starts. In this process, emulsion droplets act as templates for the obtaining of the particles, by guiding the solidification process and limiting the solidification extent.

Advantageously, the method of the invention allows to reduce the aggregation of particles.

In accordance with another advantage, particles can be produced by this method with high yield, and without use of VOC or high temperature processes.

This method is particularly advantageous to prepare biocompatible and biodegradable particles containing an active substance, which may be only slightly recognised by the complement protein system and by the macrophages of the Mononuclear Phagocyte System (MPS).

Particles

As used herein, the term "particles" refers to an aggregated physical unit of solid material.

The particles according to the invention may be micro- or nanoparticles.

Microparticles are understood as particles having a median diameter $d_{50}$ ranging from 500 µm to 1 µm and more preferably from 100 µm to 1 µm, and most preferably from 10 µm to 1 µm.

Nanoparticles are understood as particles having a median diameter $d_{50}$ inferior to 1 µm and notably ranging from 0.1 µm and 0.01 µm.

As used herein, the term "median diameter $d_{50}$" refers to the particle diameter so that 50% of the volume or of the number of the particles population have a smaller diameter.

The $d_{50}$ of the particles prepared according to the invention from an emulsion containing divalent cationic ions is generally expressed by number of particles.

The $d_{50}$ of the other particles is generally expressed by volume.

The particles may also be defined by their mean diameter. As used herein, the term "mean diameter" refers to the sum of the size measurements of all measurable particles measured divided by the total number of particles measured.

The mean and the median diameter $d_{50}$ according to the invention are determined by virtue of a particle size measurement performed on the suspensions according to the method based either on "Light Diffusion" or on the "Variation of impedance between two electrodes".

More specifically, the microparticles or nanoparticles may be microspheres or microcapsules, nanospheres or nanocapsules respectively, containing an active substance.

Emulsion

As used herein, "microspheres" or "nanospheres" are matrix systems in which the active substance is homogeneously dispersed.

"Microcapsules" or "nanocapsules" are composed of a nucleus of active material coated with a layer of polymer.

As used herein, the term "emulsion" refers to a heterogeneous system of one immiscible liquid (discontinuous phase) dispersed in another fluid or liquid in the form of droplets. The size of the droplets of the emulsion may range from 10 nm to several µm, for example to 500 µm. Thus, the term "emulsion" in the context of the present invention encompasses notably miniemulsions, nanoemulsions, macroemulsions and microemulsions.

In the context of the present invention, the emulsion may be notably a liquid-liquid emulsion, or a liquid-supercritical fluid emulsion, that means that the $CO_2$ may be in supercritical conditions or in liquid state.

$CO_2$ is said to be in the supercritical conditions (SC $CO_2$) if the temperature is greater than 31° C. and its pressure greater than $73.8 \times 10^5$ Pa. SC $CO_2$ presents some properties of both liquid and gas phases. Thus, above the critical point (Tc, Pc), i.e. between Tc-1.2Tc and Pc-2Pc, the fluid properties, like density ($\rho$, kg/m$^3$), vary according to a continuum from liquid-like to gas-like. At constant temperature, an increase in pressure results in an increase in density, while for a constant pressure, an increase in temperature leads to a decrease in the density, which remains however close to a liquid density. Consequently, the density and thus the solvent power of the supercritical fluid are tuneable in a small range of pressure and temperature. The viscosity ($\eta$, Pa·s) varies like the density, but it is less dependent on temperature at constant pressure and it is 10-100 times lower than the liquid density.

The interfacial tension ($\gamma$ mN/m) between $CO_2$, notably SC $CO_2$, and the discontinuous phase is relatively low, compared with classical interfaces (oil/water) and can be tuned by the fluid density, that is by tuning pressure and temperature conditions. More the density is high and more the fluid develops interactions with the second substance, leading to a decrease of the interfacial tension $\gamma$.

Thus, the emulsion may be prepared by contacting a solvent containing a substance selected from the group consisting of a polymer, a cationic divalent ion or a mixture thereof, soluble in said solvent, with $CO_2$, under temperature and/or pressure conditions allowing to decrease the interfacial tension and thus to obtain an emulsion of the liquid solution in the $CO_2$ phase.

The emulsion may be prepared by any conventional methods which may include notably shearing, high pressure homogenization, static mixing, sonication, phase inversion induced by temperature or/and pressure.

Preferably, the solvent containing said substance is brought into contact with $CO_2$ under stirring. The stirring may be effected with a moving blade, such as an anchor or a propeller moving blade. The stirring rate may vary in a large range and is generally comprised between 200 and 2000 rpm, notably between 500 and 1500 rpm.

Continuous Phase of the Emulsion

Preferably, the emulsion prepared at step i) contains as a continuous phase, supercritical $CO_2$.

The pressure of supercritical $CO_2$ may notably range from 80 to $350.10^5$ Pa, preferably from 200 to $250.10^5$ Pa.

The temperature of the supercritical $CO_2$ may range from 32 to 50° C., preferably from 35° to 45° C.

Advantageously, this temperature does not lead to a denaturation of biopolymers or derivatives thereof such as proteins forming the particles of the invention.

Discontinuous Phase of the Emulsion

Substance Contained in the Discontinuous Phase

The substance contained in the discontinuous phase is soluble in the solvent forming discontinuous phase and insoluble in $CO_2$ in the conditions of temperature and pressure of the process according to the invention.

As used herein, the expression "the substance is soluble in the solvent and insoluble in $CO_2$ phase" means a substance which is much more soluble in the solvent than in the $CO_2$ phase. This can be estimated by the partitioning coefficient (Kp), i.e. the ratio between the concentration of the substance in the solvent and the concentration of the substance into $CO_2$. Typically, the substance exhibits a Kp higher than said 0.8. Hence, the term "insoluble" is not to be interpreted strictly and may refer to substances which are slightly soluble in the $CO_2$ phase.

The polymer may be selected among biopolymers or derivatives thereof or synthetic polymers.

As used herein, the term "biopolymer" is understood to mean a molecule found in nature, comprising more than 30 monomer units, typically comprising up to hundred of individual monomer units. Monomer units may be notably sugars, amino acids and nucleotides.

In the context of the present invention, the term "biopolymer" also includes the bio-oligomers which comprise 30 or less monomer units.

As examples of biopolymers, mention may be made of peptides, proteins (globular or fibrous) such as collagen (amino acid monomers), polysaccharides such as cellulose (sugar monomers), nucleic acid such as RNA and DNA (nucleotide monomers). Other examples of biopolymers are lignin and natural rubber.

Biopolymers may contain many different monomers such as amino acids, or consist of one or two monomers repeated many times, for example, hyaluronic acid.

As used herein, the term "derivative of a biopolymer" or "modified polymer" refers to biopolymers which have undergone a change on their backbone, such as, for example, the introduction of reactive functional groups (such as carboxyl groups or sulphuric ester groups) or the grafting of chemical entities (molecules, fluorescent compounds, aliphatic links, PEG chains, and the like), or depolymerization by physical, chemical or enzymatic methods.

Polysaccharides which are particularly suitable in the invention are or derive from D-glucose, D-galactose, D-mannose, D-fructose or fucose.

Examples of polysaccharides or derivatives thereof comprising one or more D-glucose monomer units are notably:
  cellulose or derivatives thereof such as carboxymethylcellulose, ethylcellulose, hydroxymethylcellulose, hydroxyethylcellulose, hydroxypropyl-cellulose, methylhydroxyethylcellulose or methylhydroxypropylcellulose,
  starch or derivatives thereof such as carboxymethyl-starches,
  dextran,
  cyclodextrin.

Examples of polysaccharides or derivatives thereof comprising one or more D-fructose monomer units are notably galactosan, mannan, fructosan.

An example of polysaccharides or derivatives thereof comprising one or more fucose as monomer units is fucan.

The majority of these polysaccharides comprise the elements carbon, oxygen and hydrogen.

The polysaccharides in accordance with the invention can also comprise sulfur and/or nitrogen. They can thus derive from glycoprotein or from glycolipid. Likewise, hyaluronic acid (composed of N-acetylglucosamine and glucuronic acid units), poly(sialic acid), also known as colominic acid or poly(N-acetyl-neuraminic acid), chitosan, chitin, heparin or orosomucoid comprise nitrogen, while agar, a polysaccharide extracted from marine algae, comprises sulfur in the form of hydrogen sulfate (>CH—O—SO$_3$H). Chondroitin sulfuric acid and heparin comprise both sulfur and nitrogen.

Other examples of polysaccharides or their derivatives are notably:
  alginates extracted from brown algae,
  carragheenans of lambda, iota of kappa type extracted from red algae,
  pectins extracted from lemons, apples or beetroot,
  pectates which result from the demethylation of pectins,
  guars or modified guars, such as carboxymethylguars,
  xanthans.

Mention may be made, as illustration of the polysaccharides which are more particularly suitable in the invention, of polydextroses, such as dextran, chitosan, pullulan, starch, amylose, amylopectin, cyclodextrin, hyaluronic acid, heparin, cellulose, pectin, alginate, curdlan, fucan, succinoglycan, chitin, xylan, xanthan, arabinan, carragheenan, poly(glucuronic acid), poly(N-acetyl-neuraminic acid), poly(mannuronic acid) and their derivatives (such as, for example, dextran sulfate, amylose esters, cellulose acetate, pentosan sulfate, and the like).

Examples of proteins or derivatives thereof include notably albumins, globulins, gelatin, casein, tubulin, actin, collagen, keratin, plant proteins (gliadin, glutenins, legumin, vicilin, convicilin, albumins).

Biopolymers are advantageously biodegradable and may be useful for therapeutic uses.

As used herein, the term "synthetic polymer" refers to a large molecule typically comprising up to thousand individual monomer units which may be identical or different. Thus, the term "synthetic polymer" includes homopolymers or copolymers.

Preferably, the synthetic polymer is biodegradable, which, according to the invention, means a polymer in which the degradation may result from the action of natural chemical reactions like hydrolysis or with the help of procaryote or eucaryote cells.

According to another preferred embodiment, the polymer is biocompatible.

As used therein, "biocompatible polymer" refers to those polymers which are, within the scope of sound medical judgement, suitable for contact with the tissues of human beings and animals without excessive toxicity, irritation, allergic response, or other problem complications commensurate with a reasonable benefit/risk ratio.

Examples of synthetic polymers include notably:
  acrylic polymers or derivatives thereof such as polyacrylic or polymethacrylic acid, polyesters of acrylic or methacrylic acid (such as Poly(Methyl MethAcrylate) (PMMA)),
  polyacrylamide,
  polyalkylcyanoacrylates,
  vinyl polymers and derivatives thereof such as polymers of vinyl esters (for example, poly(vinyl acetate) or copolymers of ethylene and of vinyl acetate), polyvinyl alcohols,
  polyolefins such as polyethylene, polypropylene,
  polyamides,
  polyamides esters,
  polyalkylenes esters,
  poly(alpha-hydroxy acid)s,
  poly(beta-hydroxy acid)s,
  polylactic acid and its copolymers, such as homopolymers and copolymers of lactic and glycolic acids,
  polyanhydrides,
  polydimethylsiloxane, poly(ε-caprolactone) and its derivatives, poly(β-hydroxybutyrate, poly(hydroxyvalerate) and (β-hydroxybutyrate-hydroxyvalerate) copolymers, or poly(malic acid), amphiphilic block polymers of poly(lactic acid)-poly(ethylene oxide) type, saturated polyesters (poly(ethylene terephtalate)), polyanhydrides, polyorthoesters and polyphosphazenes.

These synthetic polymers, biopolymers or derivatives thereof which are chosen in order to be effective matrix forming and/or coating agents, may exhibit a molar mass of greater than $10^3$ g/mol, preferably of greater than $2 \times 10^3$ g/mol and more particularly of between $2 \times 10^3$ and $2 \times 10^6$ g/mol. Preferably, the concentration of the polymer is under the saturation concentration of the solvent by the polymer.

Solvent of the Discontinuous Phase

A suitable solvent according to the invention is a solvent which, under certain conditions of pressure and temperature, is chemically inert with regard to the polymer, the divalent cationic ion or the active substance, and has physical and chemical properties that make it possible to obtain an emulsion of solvent in $CO_2$ liquid and/or supercritical.

The solvent is preferably a polar solvent which is able to solubilize the substances, including the active substances, present in the discontinuous phase.

It may be selected among protic or aprotic solvents, organic solvents or water.

The solvent is preferably biocompatible.

As used herein "biocompatible" refers to those solvents which are, within the scope of sound medical judgement, suitable for contact with the tissues of human beings and animals without excessive toxicity, irritation, allergic response, or other problem complications commensurate with a reasonable benefit/risk ratio.

Examples of suitable biocompatible solvents are notably water, tetraglycol, low molecular weight polyethylene glycol, propylene glycol, water and tetraglycol being particularly preferred.

Tetraglycol is also called glycofurol or Tetrahydrofurfurylpolyethylene-glycol, Tetrahydrofurfuryl Alcohol Polyethyleneglycol Ether (CAS: 9004-76-6).

The weight of solvent may represent 0.02% to 20% of the weight of supercritical or liquid fluid.

Active Substance

The obtained particles can possess a biological activity, either because of the nature of the polymer from which they are formed or because they additionally incorporate an active substance.

In a preferred embodiment, the discontinuous phase further comprises one or more active substance(s).

The active substance may be soluble or insoluble in the solvent of the discontinuous phase. Preferably, the active substance is added in the solution of the discontinuous phase before bringing it into contact with the $CO_2$ phase.

As examples of active substances which may be contained in the microparticles of the invention, mention may particularly be made, without limitation of pharmaceutical, cosmetic, diagnostic, veterinary, food-processing, phytosanitary active substance.

Other examples of active substances suitable according to the invention are notably additives for plastics, synthetic rubbers, thermosetting resins, latex and dispersion, ink and textiles.

Examples of pharmaceutical products include notably, antipyretics, aspirin and derivatives, antibiotics, anti-inflammatories, antiulceratives, antihypertensives, neuroleptics, anti-depressants, analgesics, antifungics, antiviral, antitumorous agents, immunomodulators, antiparkinsonian, nucleotides, oligonucleotides, peptides, proteins, radionucleides.

Examples of cosmetic active substances include notably self-tanning or anti-UV agents.

Examples of processed foodstuffs are notably vitamins.

Examples of veterinary products include notably hormones, vaccines, anti-inflammatories, antibiotics.

Examples of phytosanitary active substances are notably herbicides, bactericides, fungicides, insecticides, acaricides or regulators of growth.

It is also possible to incorporate, in the particles, compounds with a diagnostic purpose. They can thus be substances emitting electromagnetic rays or substances detectable by X-ray, ultrasound or nuclear magnetic resonance. The particles can thus include iron oxide particles, such as magnetite or maghemite, gadolinium chelates, radio-opaque materials, such as, for example, air or barium, or fluorescent compounds, such as rhodamine or nile red, or gamma emitters, for example indium or technetium.

Surfactants

The emulsion droplets according to the invention can be stabilized by using surfactant molecules. Surfactants may indeed reduce the interfacial tension (γ) and consequently the interfacial free energy (GS).

Preferably, the surfactant has a cloud point pressure and a cloud point temperature which are respectively lower to the conditions of pressure and superior to the conditions of temperature used in the method according to the invention.

The surfactant may be solubilized in the $CO_2$ phase before bringing the liquid (i.e. the solvent containing a substance selected from the group consisting of a polymer, a divalent cationic ion or a mixture thereof) intended to form the discontinuous phase into contact with it.

As an example of suitable surfactants, mention may be made of the group having, fluorocarbones, polydimethylsiloxanes, siloxanes and polycarbonates tails.

Preferably, the fluorocabone surfactant is a compound of formula (I)

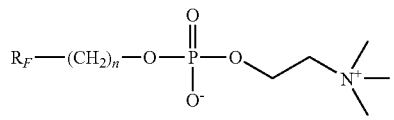

formula (I)

wherein
$R_f$ is a poly- or perfluoro-$(C_4$-$C_{12})$alkyl,
n is 1 to 15.

Such surfactants have been disclosed in Riess et al. (U.S. Pat. No. 5,344,930) and Krafft et al., 1990.

Advantageously, the aqueous droplets once formed in the $CO_2$ phase are then protected against coalescence due to the great elasticity of the interfacial layer formed by the surfactant (Tewes et al., 2004).

Preferably, the surfactant is a compound of formula (I) wherein $R_f$ is a $C_8$-perfluoroalkyl group and n is 5 (called 5-(F-octyl)pentyl][2'-N,N,N trimethylaminoethyl]phosphate) or $F_8C_5PC$, or 11 (called 11-(F-octyl)-undecyl][2'-N,N,N trimethylaminoethyl]phosphate) or $F_8C_{11}PC$.

Formation of Particles Via a Water-in-Carbon Dioxide Emulsion

According to a particularly preferred embodiment the solvent of the discontinuous phase is water.

The water preferably further comprises an aqueous buffer, which means salts having a buffering power.

Examples of suitable buffer include notably TRIS (Tris (Hydroxymethyl) Aminomethan) buffer, phosphate or bicarbonate buffer, glycin/NaCl buffer. The concentration of these buffers is such that the pH in the aqueous droplets of the emulsion can be maintained in a range of 7 to 10, during the solidification process. Typically, the concentration may range from 0.1 mol/L to 1 mol/L.

In a preferred aspect of the invention, the polymer is a biopolymer or derivative thereof, notably a protein or a polysaccharide, for example hyaluronic acid or ovalbumin.

In one embodiment, the solidification of the discontinuous phase in step ii) comprises the addition of a reticulating agent.

The reticulating agent is preferably soluble in the liquid or supercritical $CO_2$.

Examples of suitable reticulating agents are notably glyceraldehyde, formaldhehyde, glutaraldehyde, terephtaloyl chloride, epichloridrine, genipin, enzyme like transglutaminase, tyrosinase, diamine oxydase, peroxydase.

The solidification process seems to result from an interfacial reaction between the reticulating agent, which is present in the continuous phase, and the biopolymer which is present in the discontinuous phase.

According to another preferred embodiment, the discontinuous phase further comprises a divalent cationic ion $M^{2+}$.

As examples of divalent cations, mention may be made of $Ca^{2+}$, $Fe^{2+}$, $Mg^{2+}$, $Mn^{2+}$, $Zn^{2+}$, $Li^{2+}$, $Al^{2+}$, $Ni^{2+}$, $Cd^{2+}$, $Ti^{2+}$, $Co^{2+}$, $Ba^{2+}$, $Cs^{2+}$, $Cu^{2+}$; among these $Ca^{2+}$ is particularly preferred.

As a source of divalent cationic ion, metal hydroxides may be used. As an example, calcium hydroxide ($CaOH_2$) may be used as a source of $Ca^{2+}$.

The concentration of the divalent cationic ions is preferably close to the saturation concentration of $M^{2+}$ in the solvent at the pH of the discontinuous phase, at least at the beginning of the solidification process. Typically, the concentration of $M^{2+}$ may vary from 0.5 to 5% by weight of the total weight of the discontinuous phase.

Preferably, the pH in the droplets of the discontinuous phase allows the formation of $CO_3^{2-}$ ions from the solvatation of $CO_2$ molecules in the discontinuous phase. Preferably, the pH ranges from 7 to 10 and more preferably from 8 to 9.

According to a possible mechanism, the inventors have shown that the $MCO_3$ particles production results from two competitive phenomena: the emulsification of the aqueous solution by the $CO_2$ phase and the formation of $MCO_3$ solid crystals.

The $MCO_3$ crystallization phenomenon is performed in several steps.

Firstly, the diffusion of the $CO_2$ molecules into the alkali buffered solutions is accompanied by the formation of several ionic species due to its combination with the $HO^-$ ions and, if the pH decreases, with the $H_2O$ molecules, as defined by the following equations:

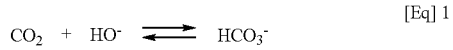
[Eq] 1

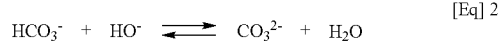
[Eq] 2

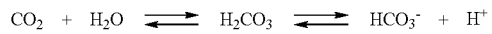
[Eq] 3

The proportion of the different species present in the solution depends on the pH. In the alkaline region, $CO_3^{2-}$ and $HCO_3^-$ species predominate.

Secondly, the $CO_3^{2-}$ ions react with the $M^{2+}$ ions, leading to the formation of $MCO_3$.

[Eq] 4

For example, $CaCO_3$ salts which have a very low aqueous solubility (~0.0013 g in 100 g of water) crystallize under various forms (calcite, aragonite, vaterite, hydrates . . . ) depending on the initial conditions (Kitamura et al.; 2002; Hostomsky, 1991; Tai, 1993; Tai, 1995; Kitamura, 2002).

The pH may also influence the formation of $MCO_3$ particles.

Indeed, $CO_3^{2-}$ ions, which contribute to the precipitation process, are only present from a pH higher than 8 (Rigopoulos et al., 2003).

This implies that, after the occurrence of a pH diminution in the process, induced by the combination of the $CO_2$ with $HO^-$ or $H_2O$ ([Eq]1-3), the $CO_3^{2-}$ molecules are no longer present, and the $MCO_3$ precipitation is terminated. Moreover, the acidic pH leads to the $MCO_3$ dissolution.

On another hand, the pH of the solution also controls the $M^{2+}$ concentration due to the reaction between the $M^{2+}$ and the $HO^-$, leading to the formation of solid $M(OH)_2$ when the ionic product (IP) is higher than the solubility product constant (Ks) of the reaction, as described by the equation 5. Therefore, the formation of $M(OH)_2$ is enhanced when the pH increases, leading to a decrease in the $M^{2+}$ concentration.

[Eq] 5

Consequently, a too high pH decreases the $M^{2+}$ concentration in the aqueous solution, whereas a too low pH leads to the decrease in the $CO_3^{2-}$ concentration. These two species are the basis of the crystallization process and their presence strongly depends on the pH. Therefore, it is advantageous to precisely and strongly buffer the aqueous solution at the right pH value, in order to control the process.

The emulsification process results in the formation of aqueous droplets dispersed in the $CO_2$ phase.

In the formation of $MCO_3$ particles, the inventors have demonstrated that the pressure of $CO_2$ both play a role of discontinuous phase and of reactant leading to the solidification of the discontinuous phase.

Indeed, it is particularly preferred that the emulsification step occurs before the crystallization, as emulsion droplets are the templates that control the crystallization and thus, the particle formation. When a surfactant is present, more quickly the surfactant molecules are adsorbed at the interface, more quickly stable droplets are formed. This aspect is favoured by the low viscosity of the $CO_2$ phase in the conditions according to the invention, which enhances the adsorption rate of the surfactant molecules.

The crystallization and emulsification phenomena are both controlled by the $CO_2$ pressure in an opposite way. In fact, the increase in the $CO_2$ pressure leads to an increase in the emulsification efficiency and emulsion stability due to the diminution in the difference between the densities of the $CO_2$ and aqueous phases and due to the reduction of the interfacial tension.

On the other hand, the increase in the $CO_2$ pressure leads to an increase in the solubility of the $CO_2$ in the aqueous phase, due to the equilibration of the $CO_2$ fugacity between the gas $CO_2$ phase and the water phase. Unfortunately, an excess of $CO_2$ dissolved in the aqueous phase results in $MCO_3$ decomposition due to the decrease of the pH as described in equation 6.

$$MCO_3 + CO_2 + H_2O \rightleftharpoons 2HCO_3^- + M^{2+} \quad [Eq]\ 6$$

Therefore, the $CO_2$ pressure is preferably precisely controlled in a range of pressures allowing the obtaining of the most stable W/C emulsion, controlling in the same time the quantity of dissolved $CO_2$ in the water phase.

The $CO_2$ pressure can be adapted according to the concentration of the buffer molecules in the discontinuous phase in order to maintain a pH allowing the latest reaction.

The particles of polymer $MCO_3$ prepared according to the invention are generally microspheres.

The morphology of particles of polymer/$MCO_3$ may vary according to the pH of the aqueous droplets of the emulsion and to the nature of the polymer and cation used.

The difference in the particles shape obtained at pH 9 to 8 can result from a competitive effect between the crystallization and emulsification phenomena.

The polymer being generally homogeneously solubilized in the aqueous droplet, the crystallization of $MCO_3$ is generally uniform, leading to spherical microspheres.

The particles obtained from a water in carbon dioxide emulsion can be lyophilized, notably after their washing.

Typically, the particles formed via a water-in-$CO_2$ emulsion have a narrow size distribution, with a mean diameter by volume or by number ranging from 0.1 μm to 10 μm.

Formation of Particles Via an Organic Solvent in Carbon Dioxide Emulsion

In a further aspect of the invention, the discontinuous phase is an organic solvent.

Suitable organic solvents according to the invention are solvents which become, for given conditions of pressure and temperature and/or in admixture with another solvent, miscible with either liquid or supercritical $CO_2$, thus allowing its extraction and the solidification of the polymer.

The organic solvent is preferably also partly or highly miscible with water.

Examples of suitable solvents are notably, tetraglycol, low molecular weight polyethylene glycol, propylene glycol.

Preferably, the solvent is tetraglycol.

Preferably, the polymer is a synthetic polymer, more preferably a polymer of lactic acid or a copolymer of lactic acid and glycolic acid.

According to this aspect of the invention, the solidification of the discontinuous phase is performed by extracting the solvent from the discontinuous phase, thus desolvating the polymer and solidifying the discontinuous phase.

In one embodiment of the invention, the solvent is extracted by adding a second solvent, said second solvent being miscible with the solvent of the discontinuous phase and not being a solvent of the substances contained in the discontinuous phase, thereby forming a mixture of solvents which is miscible in the continuous phase.

Preferably, the second solvent is water or propylene glycol

In another embodiment, the solvent is extracted from the discontinuous phase by bringing the supercritical $CO_2$ in liquid state. This can be done by reducing the temperature and the pressure so as to desolvate the polymer in a controlled way. When temperature is lower than Tc, the pressure may be increased to enhance the organic solvent extraction.

The expression "in a controlled way" is understood to mean the fact that the system is always under conditions close to equilibrium and is not subjected to sudden variation in pressure.

Preferably, the solvent is extracted by contacting a flow of fresh liquid $CO_2$.

Preferably, the temperature of liquid $CO_2$ ranges from 10° to 20° C. and is more preferably of about 15° C.-16° C.

Preferably, the pressure of liquid $CO_2$ ranges from 80 to $160.10^5$ Pa and more preferably from 100 to $150.10^5$ Pa.

According to a further embodiment, the solvent is extracted by both adding said second solvent and bringing the supercritical $CO_2$ in liquid state.

After a substantial amount of solvent is extracted, an aqueous solution of a dispersing agent may advantageously be added so as to harden the obtained particles.

Examples of suitable dispersing agents are notably triblock copolymers of polyoxyethylene-polyoxypropylene-polyoxyethylene known as poloxamers or Pluronic®.

Preferably, the dispersing agent is the poloxamer sold under the tradename of Pluronic F68, which is agreed by FDA.

Preferably, the method according to the invention is carried out in a closed reactor, such as an autoclave.

The obtained particles may be recovered by using conventional methods such as filtration or centrifugation and can be lyophilized after their washing.

In a further aspect, the invention is directed to dispersions of particles obtainable by the method of the invention. Preferably, the dispersion results from a water-in-carbon dioxide emulsion.

In a still further aspect, the invention is directed to particles obtainable by the method of the invention.

Preferably, the particles are microspheres or nanospheres comprising a biopolymer, $MCO_3$ and an active substance dispersed in a $MCO_3$/biopolymer matrix system. The particles may notably comprise an active substance coated with a biopolymer or a biodegradable synthetic polymer.

Typically, the mean diameter by volume or by number of the obtained particles ranges from 0.1 μm to 100 μm, preferably from 1 μm to 20 μm and more preferably from 2 μm to 5 μm.

In a still further aspect, the invention is directed to the use of particles or dispersions thereof as a vehicle for cosmetic, pharmaceutical, diagnostic, veterinary, phytosanitary or foodstuff products.

More particularly, the particles according to the invention are useful to encapsulate active substances and notably to prepare controlled drug delivery systems, such as fast or slow drug-release formulations.

As a result of the immunogenicity of certain biopolymers such as ovalbumin, the particles of the invention may be specifically captured by the cells of the immune system (macrophages) and thus may be particularly useful in the field of antitumoral vaccination or of cellular imaging.

As an example, the particles able to be captured by the immune system cells may contain proteins coming from tumours or a contrast agent as an active substance.

The particles or the dispersions thereof may also be used in further diverse applications such as:
- in paper as filler or as a retaining agent,
- in adhesives,
- in inks,
- as anticorrosion coatings,
- fragrance compositions in textiles or cosmetics.

FIGURE

FIG. 1: Schematic representation of the equipment used to formulate $CaCO_3$ particles in $CO_2$ medium. A: Bottle of $CO_2$; B: cooling system for the $CO_2$; C: pump for the $CO_2$; D: heating system; E: autoclave; F: HPLC pump.

EXAMPLES

1. Materials

Calcium hydroxide; chicken egg white albumin of grade V (OVA); bovine serum albumin-fluorescein isothiocyanate (BSA-FITC) were purchased from Sigma Aldrich, France. Tris(hydroxymethyl)aminomethan (TRIS) was purchased from Merck, France. The $CO_2$ used in the experiments is of medical grade (purity 99.99%) and was purchased from Air Liquide, France. Ultrapure water was produced by a MilliQ plus 188 apparatus (Millipore, France).

The phosphocholine-based fluorinated surfactants were synthesized according to Krafft et al., 1990. Their purity (>99%) was assessed by HPLC, NMR and elemental analysis.

The BSA (Bovine Serum Albumin) was purchased from Sigma (France).

Pluronic F68®, Lutrol F68® (poloxamer 188) (HO—$(C_2H_4O)_{80}$—$(C_3H_6O)_{27}$—$(C_2H_4O)_{80}$—H) were provided by BASF Poly($\alpha$-hydroxyacid)s such as PLA50 and PLGA 37.5/25 were purchased from Phusis (France)

Glycofurol was provided by Sigma (France)

Propylene glycol was provided by Sigma (France).

2. Methods

2.1. Microsphere Preparation

The experimental work was conducted using the apparatus presented in FIG. 1 (Separex Equipments, Champigneulles, France).

It is composed of a 500 mL autoclave having at its upper side a stirrer coupled to an internal Teflon blade. This stirrer allows mixing the content of the cell with a maximal rate of 1500 rpm. A known quantity of $CO_2$ was introduced from the top of the cell at the desired pressure and temperature. The polymer solution was brought from the bottom of the cell under a controlled flow rate and at a pressure higher than the one already existing in the autoclave.

2.2. Microsphere Size and Morphology

2.2.1. Particles Prepared from a Water-In-$CO_2$ Emulsion

The different kinds of microparticles were observed in aqueous suspension by an optical microscope (Olympus type BH-2) coupled to a CCD camera (COHU). Image captures and particles size determination were performed with the Archimed 3.9.0 software (Microvision instruments, Evry, France).

Scanning electron microscope (SEM; JEOL 6301F; Jeol France, 78000 Croissy-sur-Seine), equipped with an energy dispersive X-ray (EDX) unit, was utilized to examine the surface morphology, as well as for having an idea of the size distribution of the microspheres. Lyophilized samples of microspheres were mounted on aluminum stubs and sputter coated with a carbon layer. A voltage of 5 or 20 kV was applied.

Size measurements were performed using a Coulter® counter.

2.2.2. Particles Prepared from an Organic Solvent in $CO_2$ Emulsion

The different kinds of microparticles were observed in aqueous suspension by an optical microscope (Olympus type BH-2) coupled to a CCD camera (COHU). Image captures and particles size determination were performed with the Archimed 3.9.0 software (Microvision instruments, Evry, France).

Scanning electron microscope (SEM; JEOL 6301F; Jeol France, 78000 Croissy-sur-Seine), equipped with an energy dispersive X-ray (EDX) unit, was utilized to examine the surface morphology, as well as for having an idea of the size distribution of the microspheres. Lyophilized samples of microspheres were mounted on aluminum stubs and sputter coated with a carbon layer. A voltage of 5 or 20 kV was applied.

2.3. Composition of Spheres Prepared from a Water-In-$CO_2$ Emulsion

The elementary composition of the microspheres was determined by recording the energy dispersive X-ray (EDX) spectra collected on 60 seconds at different locations. The measurements were performed with the same apparatus as the one used for SEM experiments. The detection limit of the measurements is of 1 wt %.

The composition of the washed and lyophilized microspheres was investigated by FT-IR spectroscopy. The spectra were recorded between 4000-500 $cm^{-1}$ with a Bruker FT-IR Vector 22 using potassium bromide pellets. For each spectrum, a 20-scan interferogram was collected at a resolution of 2 $cm^{-1}$. A pre-recorded water vapour absorption spectrum under identical conditions was subtracted after data collection. Prior to obtaining the sample spectrum, an open beam background spectrum was recorded.

2.4. Particle Zeta Potential Measurements

The zeta potential ($\zeta$) of various kinds of $CaCO_3$ particles was measured under a voltage of 100 mV using a Zetasizer 2000 (Malvern). This value was measured for suspensions having approximately the same particle concentration. A single point measurement was conducted for a pH of 8 and under a conductivity of 400 µS/cm, adjusted by a 0.5 M TRIS buffer. Each value represents the average between fifteen measurements.

2.5. FITC-BSA Microsphere Loading

In order to know if it is possible to encapsulate proteins into the particles, and in same time, to visualize the protein localization in the particles, the particles were formulated in presence of a fluorescent protein (BSA-FITC). The technique was identical to the one described in section 2.1. and in examples 1 to 3 hereafter, with the single difference that in the initial alkali aqueous solution containing 1 g/L of OVA, 5 mg/L of BSA-FITC were added. The particles were analyzed by fluorescent microscopy (Zeiss Axiotop 2 MOT, UV Zeiss type Atto Arc 2 HBO 100 W lamp) with an excitation wavelength of 488 nm and an emission wavelength of 519 nm, corresponding to the FITC-labelled substrate.

2.6. Biocompatibility Study

The complement system is involved in the opsonisation of the foreign object. The activation of the complement system by the microparticles was studied by a technical method called "CH50 modified method" (Mayer et al., 1961; Kazatchkine et al., 1986; Passirani et al., 1998).

3. Examples 1 to 3

Particles of Biopolymers 3.1. Examples 1 and 2: Particles of $CaCO_3$/Biopolymers Step 1: Solubilization of the Surfactant in the $CO_2$ Phase (Optional Step)

The surfactants which were used in this procedure for the formation of particles of $CaCO_3$ were fluorinated surfactants such as $F_8C_5PC$ or $F_8C_{11}PC$ (Prof. M P Krafft, Institut Charles Sadron, Strasbourg, France) (Riess et al., U.S. Pat. No. 5,344,930; M. P. Krafft et al., 1990).

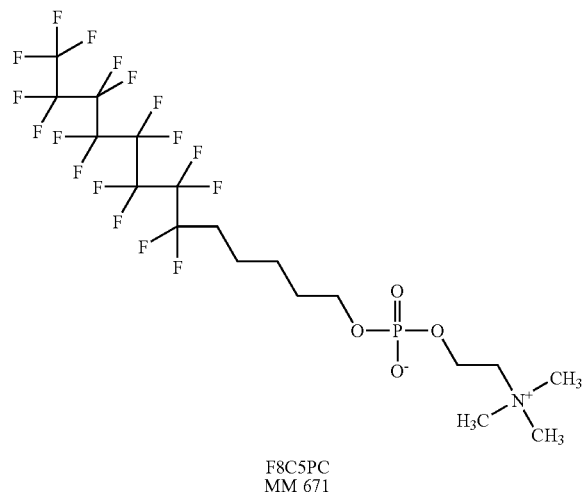 [SMILES: C[N+](C)(C)CCOP(=O)([O-])OCCCCCC(F)(F)C(F)(F)C(F)(F)C(F)(F)C(F)(F)C(F)(F)C(F)(F)C(F)(F)F]

F8C5PC
MM 671

These surfactants have a fluorinated chain, a phosphocholin group and a linker comprising 5 or 11 carbon atoms.

An amount of surfactant (0 to 50 mg) was added in the reactor of 500 ml, thermostatically controlled at 25° C.

Under stirring with a propeller or anchor moving blade (300-400 rpm), the $CO_2$ was introduced in the autoclave up to a pressure of $200.10^5$ Pa. This step of solubilization of surfactant was performed during at least 10 minutes.

Remark: This step is optional since it is possible to formulate particles of $CaCO_3$ and of biopolymer without surfactant.

Step 2: Addition of the Aqueous Phase

The aqueous phase was composed of 3 elements:

a) an aqueous buffer to maintain the pH in a determined range (basic pH=8-10), 2 types of buffer were used to maintain the basic pH at concentration ranging from 0.5 to 1 mol/L: TRIS buffer, and Glycin/NaCl buffer;

b) calcium hydroxide ($CaOH_2$) as a source of $Ca^{2+}$ for the formulation of calcium carbonate in concentrations which were comprised between 0.5 and 1%;

c) a biopolymer which plays a role of matrix wherein the crystallization of $CaCO_3$ occurs and which allows to structurate the final form of the microparticle.

Ovalbumine grade VII (protein) and hyaluronic acid (polysaccharide) at concentrations of 1 g/L were used in these experiments. The addition of the aqueous phase was effected in one or two steps.

Addition in one step: once the surfactant was completely solubilized, 25 mL of aqueous solution containing the three elements (a), (b) and (c) were added in the autoclave under continuous stirring at 1000 rpm at a flow rate of 10 mL/min leading to a final pressure in the cell ranging form 220 to $240.10^5$ Pa. After adding the total volume, the stirring was then continued during 5 minutes because for larger times, the pH decreases to a level that results in the decomposition of the $CaCO_3$ particles into a soluble salt.

Two steps addition: once the surfactant was completely solubilized, 25 mL of a solution of a biopolymer at 1 g/L in a buffer solution were added in the autoclave with a flow rate of 10 mL/min and by setting the stirring rate at 1000 rpm. The stirring was continued during 5 minutes then 15 mL of a solution of $Ca(OH)_2$ at 1% in an identical buffer were then administered in the reactor. The speed rate was continued at a stirring rate of 1000 rpm during 5 minutes. The final pressure in the autoclave was comprised between 240 and 260 bars.

Step 3: Depressurizing the Autoclave

At the end of the processes, the stirring was stopped and the autoclave was slowly depressurized (−40 to $50.10^5$ Pa/min).

Step 4: Recovering the Microparticles

The suspension of microparticles was centrifuged at 4000 rpm during 15 minutes.

The centrifugation pellet was taken with 40 mL of demineralised water, then centrifuged again at 4000 rpm during 15 minutes. This rinse was effected 3 times. The centrifugation pellet of microparticles was finally taken with 2 mL of demineralized water and lyophilized to obtain a dry powder of microparticles.

Example 1

Particles of $CaCO_3$/Ovalbumine Grade (VII)

The above procedure was applied with the following conditions.

Formulation
  10 mg of surfactant $F_8C_5PC$
  25 mL of aqueous solution comprising $Ca(OH)_2$ at 0.5% and Ovalbumine grade VII 1 g/L in a TRIS buffer 0.5 M, pH=8.4.

Process
  Addition in one step
  Final pressure=$235.10^5$ Pa

Yield
  Mean yield=115 mg per formulation (by autoclave)

Measurement of the size with Coulter® Multisizer

This method used to determine the particles diameter is based on the variation of impedance when a particle goes through between 2 electrodes.

The measurement of the size was effected after dispersing the particles in a ISOTON-Tween 1% medium.

The statistical results were as follows

TABLE 1

| Statistical results of the measurements of the size with Coulter ® Multisizer for the studied formulation. | |
|---|---|
| Mean (μm) | 2.92 |
| Standard deviation (μm) | 2.67 |
| d 10 (μm) | 0.87 |
| d 50 (μm) | 1.97 |
| d 90 (μm) | 6.38 |

Differential Scanning Calorimetry (DSC)

A DSC analysis was realized on the formulation and on each of the components of the microparticle, that is ovalbumin, $CaCO_3$, and the fluorinated surfactant. The DSC profile of the microparticles displayed a signal around 155-158° C., a signal that corresponds to ovalbumin VII. The signal corresponding to the surfactant was not detected as it was present in too low amounts.

This study thus allowed to conclude that the formulated particles contain ovalbumin in their structure.

Study of the activation of the complement (biocompatibility study).

Results obtained by measuring the CH50 consumption versus surface showed that $CaCO_3$ particles were significantly less active than control particles (sephadex G50).

Example 2

Particles of $CaCO_3$/Hyaluronic Acid

Particles of $CaCO_3$/Hyaluronic Acid were prepared according to example 1, with or without the surfactant $F_8C_{11}PC$.

The results obtained with the Coulter® Multisizer showed that the use of a surfactant had no influence in the size of the particles. The particles obtained without surfactant display a mean diameter 2 times superior than those obtained with a surfactant.

TABLE 2

Statistical results of the measurements of the size with Coulter ® Multisizer for formulations of microparticles $CaCO_3$/Hyaluronic acid with or without surfactant.

|  | Formulation with a surfactant | Formulation without surfactant |
|---|---|---|
| Mean (μm) | 2.40 | 5.86 |
| Standard deviation (μm) | 2.25 | 4.05 |
| d 10 (μm) | 0.85 | 1.52 |
| d 50 (μm) | 1.05 | 4.70 |
| d 90 (μm) | 5.99 | 12.2 |

It was experimented to encapsulate BSA-FITC into $CaCO_3$ particles in order to demonstrate the location of the protein inside or at the surface of the microspheres, by using the method described in section 2.5. with OVA as template for particle obtaining and by buffering the pH at a value of 8. According to the analysis of the transmission optical micrograph, the obtained particles had a size of about 1 μm and kept the distribution obtained without BSA-FITC. Further, according to the fluorescence optical micrograph, the protein was encapsulated in the microspheres as revealed by the fluorescent spots, which coincide with the microspheres of the transmission optical micrograph. Identically encapsulation was obtained in the absence of two surfactants or by proceeding with a one step or two steps addition of the aqueous solution.

3.2. Example 3: Microparticles of Ovalbumin 3.2.1. Microparticles Preparation

Microparticles of ovalbumin were prepared according to the following method.

Step 1: Solubilization of the Surfactant in the $CO_2$ Phase 10 to 20 mg of fluorinated surfactant was added in the autoclave of the reactor, thermostatically controlled at a temperature of 40° C.

The $CO_2$ was then introduced in the autoclave under stirring with a moving blade up to a pressure of $270.10^5$ Pa.

Step 2.: Addition of the Aqueous Phase

Once the surfactant was completely solubilized, 1 mL of a ovalbumin solution was added under continuous stirring (1500 rpm, at a flow rate of 10 mL/min leading to a final pressure ranging from 200 to $300.10^5$ Pa). After adding the total volume, the stirring was continued during 1 hour at 1500 rpm.

Step 3.: Addition of Reticulating Agent 1 mL of glyceraldehyde under a flow rate of 10 mL/min or 20 mg of terephtaloyl chloride was added in the autoclave in order to reticulate the formed particles. In the case of terephtaloyl chloride, the ovalbumin solution in step 2 was buffered around a pH of 10.

Step 4.: Depressurizing the Autoclave

At the end of the process, the stirring was stopped and the autoclave was depressurized slowly ($30\text{-}50.10^5$ Pa/min).

Step 5.: Recovering the Microparticles

The suspension of microparticles was centrifuged at 4000 rpm during 15 minutes.

The centrifugation pellet was taken with 40 mL of demineralized water, then centrifuged again at 4000 rpm during 15 minutes. This rinse was effected three times. The centrifugation pellet of microparticles was finally taken with 2 mL of demineralized water and lyophilized to obtain a dry powder of microparticles.

3.2.2. BSA-FITC Encapsulation

The method of encapsulation disclosed in part 2.5 was applied with the following conditions:
Ovalbumin solution: 4 g/L+5 mg/L BSA-FITC in PBS pH=7.4
10 to 20 mg of fluorinated surfactant
Initial pressure $210.10^5$ Pa
Temperature=40° C.
Stirring rate=1500 rpm
1.5 mL of a solution ovalbumin and BSA-FITC
Final pressure of $280.10^5$ Pa
Time stirring=1 hour.
Reticulating agent (glyceraldehyde or terephtaloyl chloride)

By analyzing the transmission optical micrograph in visible light and in fluorescence (520 mm), fluorescent spots were observed in the particles, thus demonstrating the encapsulation of BSA-FITC.

3.2.3. Gadoteric Acid Encapsulation

The method of encapsulation disclosed in part 2.5 was applied with the following conditions:
Ovalbumin solution: 4 g/L
10 to 20 mg of fluorinated surfactant
Initial pressure 210.105 Pa
Temperature=40° C.
Stirring rate=1500 rpm
0.8 mL of ovalbumin 0.4 g/L mixed with gadoteric acid at 0.1 mol/L
Final pressure of 280.105 Pa
Time stirring=1 hour.
Reticulating agent: 0.4 mL of glyceraldehyde The obtained particles were then analyzed with an optical microscope. The particles observed were spherical with a size ranging from 1 to 10 μm.

From scanning electron microscopy spherical particles exhibited a pleat surface. From EDX analysis, gadolinium was mainly encapsulated into the particles.

4. Examples 4 and 5

Microparticles of Biodegradable Synthetic Polymers 4.1. Example 4: Microparticles of Biodegradable Polymers Prepared from an Emulsion of Tetraglycol in Supercritical $CO_2$: Solidifying the Discontinuous Phase Droplets by Adding Water

4.1.1. Microparticles Preparation

Step 1.: Solubilization of Polymer in Tetraglycol

The polymer was a polymer of lactic acid (PLA) or a copolymer of lactic and glycolic acid (PLGA) or any polymer soluble in the tetraglycol.

The polymer was solubilized in tetraglycol in order to obtain a solution of low viscosity. The percentage of polymer in the solution will depend on the molecular weight of polymer and of its solubility in tetraglycol.

Typically, a PLGA of a mean, molecular weight of 20000 g/mol was solubilized in a ratio of 2.5% to 20% (w/v) (weight/volume) in tetraglycol.

Step 2.: Emulsion=Solution of Polymer/Tetraglycol Dispersed in $CO_2$ 20 mL of the solution of polymer in tetraglycol were introduced in a reactor thermostatically controlled of 500 mL at 35° C.

Under stirring with a moving blade, $CO_2$ was added in the autoclave up to a pressure of $180.10^5$ Pa. These experimental conditions allowed to obtain an emulsion of the solution of polymer in supercritical $CO_2$.

This step, which was necessary to form and to stabilize the droplets of the solution of polymer in tetraglycol, was performed during 5 minutes.

The time of this step depended on the percentage of the polymer solubilized in tetraglycol.

Step 3. Extraction of the Organic Solvent 50 mL of the aqueous solution at 1% (w/v) of Pluronic F68 was then added at a flow rate of 10 mL/min in the autoclave. The pressure in the autoclave was then of 280.105 Pa. The addition in the solution of the dispersity agent was:
- to provide the extraction of tetraglycol, by favouring the precipitation and the hardening of the polymer;
- to prevent the agglomeration of microparticles by the presence of the dispersing agent Pluronic F68.

Step 5.: Depressurization of the Autoclave

The autoclave was then slowly depressurized (about $30\text{-}50.10^5$ Pa/min).

25 mL of an aqueous solution at 1% (w/v) of Pluronic F68 was finally added at a flow rate of 10 mL/min in the autoclave once at the atmospheric pressure.

Step 6.: Recovering Microparticles

The suspension of microparticles was centrifuged at 4000 rpm during 20 minutes.

Each pellet of microparticles was taken in 45 mL of demineralised water, then centrifuged again at 4000 rpm during 10 minutes. This rinse was performed two or three times.

The pellet of microparticles was finally taken in 2 mL of demineralised water and lyophilized to obtain a dry powder of microparticles.

4.1.2. Microparticles Characterization

Microparticles obtained from a solution of PLA 50 10% (w/v) in the tetraglycol or from a solution of PLGA 37.5/25 5% (w/v) in tetraglycol were observed by an optical microscope coupled with a software (Microvision®) allowing the size estimation. These microparticles had a estimated diameter comprised between 1 µm to 10 µm.

4.2. Example 5: Microparticles of Biodegradable Synthetic Polymers from an Emulsion of Tetraglycol in Supercritical $CO_2$ Solidifying the Discontinuous Phase Droplets by Extraction with Liquid $CO_2$ and then by Addition of Water

4.2.1. Microparticles Preparation

Step 1.: Solubilization of Polymer in Tetraglycol

The polymer was a polymer of lactic acid (PLA) or a copolymer of lactic and glycolic acid (PLGA) or any polymer soluble in the tetraglycol.

The polymer was solubilized in tetraglycol in order to obtain a solution of low viscosity. The percentage of polymer in the solution will depend on the molecular weight of polymer and of its solubility in tetraglycol.

Typically, a PLGA of a mean, molecular weight of 20000 g/mol was solubilized in a ratio of 2.5% to 20% (w/v) (weight/volume) in the tetraglycol.

Step 2.: Incorporation of the Protein in the Solution

The BSA (Bovine Serum Albumine was chosen as model. It was spheronized in the presence of Lutrol F68® according to the technique disclosed by Morita et al., 2000.

The co-lyophilizate BSA-Lutrol F68 was added to the solution of polymer-tetraglycol. The Lutrol F68 can be solubilized at 37° C. in tetraglycol allowing to obtain a suspension of particles of BSA in the solution of PLGA/Lutrol F68/tetraglycol.

Step 3.: Emulsion of a Solution of Polymer/Tetraglycol in Supercritical $CO_2$ 10 mL of the suspension of BSA in the solution of polymer/Lutrol F68/tetraglycol were introduced in the reactor of 500 mL thermoregulated at 35° C. Under stirring with a propeller or anchor moving blade, the $CO_2$ is introduced in the autoclave up to a pressure superior or equal to $240.10^5$ Pa. and inferior or equal to $300.10^5$ Pa. These experimental conditions allow to obtain an emulsion of a solution of polymer/tetraglycol in the $CO_2$ in supercritical conditions.

This step, which allows the formation and the stabilization of droplets of solution polymer/tetraglycol containing particles of BSA, was performed during 10 to 12 nm, time necessary to obtain a pressure of $240.10^5$ Pa. in the autoclave.

Step 4.: Extraction in $CO_2$ Liquid Phase at 15° C.

While maintaining the stirring, the temperature of the middle was decreased at 15° C., the $CO_2$ then became liquid. The decrease of the temperature of the middle led to a decrease of the pressure which was stable between 100 and $150.10^5$ Pa. when the temperature of the middle was at 15-16° C. Under these conditions of pressure and temperature, the $CO_2$ was in liquid state, allowing an extraction of the part of tetraglycol and the precipitation of the polymer as microparticles, around particles of BSA.

The extraction phase (at 15° C. and $100\text{-}150.10^5$ Pa.) was performed during at least 30 nm.

Step 5.: Microparticles Curing 25 or 50 mL of an aqueous solution containing 1% (w/v) of Pluronic F68 were then added to a flow of 10 mL/mn in the autoclave. The pressure in the autoclave was then at least of $200.10^5$ Pa.

The addition of an aqueous solution of surfactant aimed at:
- achieve the extraction of tetraglycol, favourizing the precipitation and the hardening of the polymer,
- preventing the agglomeration of microparticles by the presence of the surfactant Pluronic F68.

Step 6.: Depressurizing the Autoclave

The autoclave was then slowly depressurized (about 30-50.105 Pa/min).

25 mL of an aqueous solution at 1% (w/v) of Pluronic F68 was finally added at a flow rate of 10 mL/min in the autoclave once at the atmospheric pressure.

The suspension of microparticles was then introduced in 100 or 150 mL of demineralised water under stirring to complete the extraction.

Step 7.: Recovering Microparticles

The suspension of microparticles was centrifuged at 4000 rpm during 20 minutes.

Each pellet of microparticles was taken in 45 mL of demineralised water, then centrifuged again at 4000 rpm during 10 minutes. This rinse was performed two or three times.

The pellet of microparticles was finally taken in 2 mL of demineralised water and lyophilized to obtain a dry powder of microparticles.

4.2.2. Microparticles Characterization

Microparticles obtained from a solution of PLGA 37.5/25 5% (w/v) in tetraglycol were observed by an optical microscope coupled with a software (Microvision®) allowing the size estimation. These microparticles had a estimated diameter comprised between 1 μm to 15 μm.

Under fluorescent microscopy FITC-BSA microparticles of PLGA 37.5/25 showed a typical fluorescence indicating the incorporation of the protein inside the particles.

REFERENCES

Arshady, R. *Journal of Controlled Release* 1991, 17, 1-21

Bartscherer, K. A.; Minier, M.; Renon, H. *Fluid Phase Equilibria* 1995, 107, 93-150

Benoit, J. P.; Marchais, H.; Rolland, H.; Van de Velde, V. In *Microencapsulation: Methods and Industrial Applications*; Benita, S., Ed.; Marcel Dekker, Inc, 1996, pp 35-72

Campbell, M. L.; Apodaca, D. L.; Yates, M. Z.; McCleskey, T. M.; Birnbaum, E. R. *Langmuir* 2001, 17, 5458-5463 da Rocha, S. R. P.; Dickson, J.; Cho, D.; Rossky, P. J.; Johnston, K. P. *Langmuir* 2003, 19, 3114-3120

Eastoe, J.; Cazelles, B. M. H.; Steytler, D. C.; Holmes, J. D.; Pitt, A. R.; Wear, T. J.; Heenan, R. K. *Langmuir* 1997, 13, 6980-6984

Harrison, K.; Goveas, J.; Johnston, K. P.; O'Rear, E. A. *Langmuir* 1994, 10, 3536-3541

Hoefling, T.; Enick, R.; Beckman, E. *J. Phys. Chem. B* 1991, 95, 7127

Hostomsky Journal Physics D: Applied Physics 1991, 24, 165-170, Tai *AIChE Journal* 1993, 44, 1790-1798

*ICH Harmonized Tripartite Guideline for Residual Solvents*, step 4, 1997

Jacobson, G. B.; Ted Lee Jr., C.; Johnston, K. P.; Tumas, W. *Journal of the American Chemical Society* 1999, 121, 11902-11903

Johnston, K. P.; Cho, D.; DaRocha, S. R. P.; Psathas, P. A.; Ryoo, W.; Webber, S. E.; Eastoe, J.; Dupont, A.; Steytler, D. C. *Langmuir* 2001, 17, 7191-7193

Kane, M. A.; Baker, G. A.; Pandey, S.; Bright, F. V. *Langmuir* 2000, 16, 4901-4905

Kazatchkine M D, Hauptmann G, Nydegger U E. Techniques du complément. Paris:Inserm, 22-23; 1986

Kitamura, M.; Konno, H.; Yasui, A.; Masuoka, H. *Journal of Crystal Growth* 2002, 236, 323-332

Krafft, M. P.; Rolland, J. P.; Vierling, P.; Riess, J. G. *New J. Chem.* 1990, 14, 869-875

Lee Jr, C. T.; Psathas, P. A.; Johnston, K. P.; deGrazia, J.; Randolph, T. W. *Langmuir* 1999, 15, 6781-6791

Mayer M M. Experimental Immunochemistry. Springfield, Ill., USA: Thomas; 1961. 133-156;

Mendes, R. L.; Nobre, B. P.; Cardoso, M. T.; Pereira, A. P.; Palavra, A. F. *Inorganica Chimica Acta* 2003, 356, 328-334

Morita et al., Pharmaceutical Research, vol. 17, n° 11, 2000

O'Neill, M. L., et al., *Emulsion Stabilization and Flocculation in $CO_2$. 1. Turbidimetry and Tensiometry*. Macromolecules, 1997. 30: p. 5050-5059

O'Neill, M. L., et al., *Solubility of Homopolymers and Copolymers in Carbon Dioxide*. Ind. Eng. Chem. Res., 1998. 37: p. 3067-3079

Ozcan, A.; Ozcan, A. S. *Talanta* 2004, 64, 491-495

Passirani C., Barratt G., Devissaguet J. P., Labarre D., Interactions of nanoparticles bearing heparin or dextran covalently bound to poly(methyl methacrylate) with the complement system. Life Sci 1998; 62(8):775-85

Psathas, P. A.; da Rocha, S. R. P.; Lee, C. T. J.; Johnston, K. P.; Lim, K. T.; Webber, S. *Ind. Eng. Chem. Res.* 2000, 39, 2655-2664

Psathas, P. A.; Janowiak, M. L.; Garcia-Rubio, L. H.; Johnston, K. P. *Langmuir* 2002, 18, 3039-3046

Rigopoulos, S.; Jones, A. *Ind. Eng. Chem. Res.* 2003, 42, 6567-6575 Riess J. G., Jeanneaux, F., Krafft M. P., Santaella C., Vierling P., U.S. Pat. No. 5,344,930

Da Rocha, S. R. P., K. L. Harrison, and K. P. Johnston, *Effect of Surfactants on the Interfacial Tension and Emulsion Formation between Water and Carbon Dioxide*. Langmuir, 1999.15: p. 419-458

Ryoo, W.; Webber, S. E.; Johnson, K. P. Ind. Eng. Chem. Res. 2003, 42, 6348-6358

Saldana, M. D. A.; Mohamed, R. S.; Mazzafera, P. *Fluid Phase Equilibria* 2002, 194-197, 885-894

Sun, Q.; Deng, Y. *Journal of Colloid and Interface Science* 2004, 278, 376-382 Tai *AIChE Journal* 1995, 41, 68-77, Kitamura *Journal of Crystal Growth* 2002, 237-239, 2205-2214

Tewes, F.; Boury, F. *J. Phys. Chem. B* 2004, 108, 2405-2412

Tewes, F.; Butoescu, N.; Krafft, M. P.; Boury, F. submitted 2004

Tomasko D L, Li H, Liu D, et al. A review of $CO_2$ applications in the processing of polymers. Ind Eng Chem Res 2003; 42:6431-6456.

Zielinski, R. G.; Kline, S. R.; Kaler, E. W.; Rosov, N. *Langmuir* 1997, 13, 3934-393

The invention claimed is:

1. A method for preparing particles comprising the steps of:
  i) preparing an emulsion containing:
    a continuous phase comprising supercritical $CO_2$ or liquid $CO_2$, and
    a discontinuous phase comprising an active substance and a solvent containing a substance selected from the group consisting of a polymer, a divalent cationic ion and a mixture thereof, said substances being soluble in said solvent and insoluble in said continuous phase, and said solvent being immiscible with said continuous phase; wherein the emulsion is prepared by contacting said solvent with $CO_2$ under temperature and/or pressure conditions that allow decrease of interfacial tension so as to obtain an emulsion in the $CO_2$ phase; and
  ii) solidifying said discontinuous phase, thereby forming particles encapsulating said active substance.

2. The method of claim 1, wherein, in step i) the emulsion contains as a continuous phase supercritical $CO_2$.

3. The method of claim 1, wherein the solvent is biocompatible.

4. The method of claim 1, wherein the active substance is selected from pharmaceutical, diagnostic, cosmetic, veterinary, phytosanitary products, or processed foodstuffs.

5. The method of claim 1, wherein the polymer is a biopolymer or derivatives thereof, or a synthetic polymer.

6. The method of claim 5, wherein the biopolymer is or derives from a peptide, a protein, a polysaccharide or nucleic acids.

7. The method of claim 5, wherein the synthetic polymer is a biodegradable polymer.

8. The method of claim 6, wherein the solvent is water.

9. The method of claim 8, wherein the water further comprises an aqueous buffer.

10. The method of claim 8, wherein the solidification of the discontinuous phase comprises the addition of a reticulating agent.

11. The method of claim 1, wherein the divalent cationic ion is selected from the group consisting of $Ca^{2+}$, $Fe^{2+}$, $Mg^{2+}$, $Cu^{2+}$ $Mn^{2+}$, $Zn^{2+}$, $Li^{2+}$, $Al^{2+}$, $Ni^{2+}$, $Cd^{2+}$, $Ti^{2+}$, $Co^{2+}$, $Ba^{2+}$, and $Cs^{2+}$.

12. The method of claim 8, wherein the emulsion further comprises a surfactant.

13. The method of claim 7, wherein the solvent is an organic solvent.

14. The method of claim 13, wherein the solvent is tetraglycol.

15. The method of claim 13, wherein the polymer is a polymer of lactic acid or a copolymer of lactic acid and glycolic acid.

16. The method of claim 13, wherein the solidification of the discontinuous phase is performed by extracting the solvent.

17. The method of claim 16, wherein the solvent is extracted by adding a second solvent, said second solvent being miscible with the solvent of the discontinuous phase and not a solvent for the substances of the discontinuous phase, thereby forming a mixture of solvents which is miscible in the continuous phase.

18. The method of claim 16, wherein the solvent is extracted by bringing the supercritical $CO_2$ to a liquid state.

19. The method of claim 13, wherein an aqueous solution of a dispersing agent is added to the formed particles.

20. The method of claim 1, wherein the method is carried out in a closed reactor.

21. The method of claim 1, wherein the formed particles are recovered.

* * * * *